US007780592B2

(12) United States Patent
Tronnes

(10) Patent No.: US 7,780,592 B2
(45) Date of Patent: Aug. 24, 2010

(54) DISTAL PORTION OF AN ENDOSCOPIC DELIVERY SYSTEM

(75) Inventor: Carole A. Tronnes, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 770 days.

(21) Appl. No.: 10/977,499

(22) Filed: Oct. 29, 2004

(65) Prior Publication Data

US 2006/0094929 A1 May 4, 2006

(51) Int. Cl.
*A61B 1/00* (2006.01)
*A61B 1/04* (2006.01)
*A61B 1/12* (2006.01)

(52) U.S. Cl. .................... 600/127; 600/156; 600/114

(58) Field of Classification Search ............. 600/104, 600/105, 127, 153, 156, 157, 29, 30, 120, 600/154; 604/22, 28, 35, 36, 48, 500, 57, 604/115, 164.06, 37; 606/140, 151; 424/435
See application file for complete search history.

(56) References Cited

U.S. PATENT DOCUMENTS

| 5,069,666 A * | 12/1991 | Gericke ................... 604/86 |
| 5,632,754 A * | 5/1997 | Farley et al. ............. 606/159 |
| 5,853,416 A | 12/1998 | Tolkoff |
| RE36,629 E | 3/2000 | Zaslavsky et al. |
| 6,098,629 A * | 8/2000 | Johnson et al. ........... 128/897 |
| 6,338,345 B1 * | 1/2002 | Johnson et al. ........... 128/897 |
| 6,358,197 B1 | 3/2002 | Silverman et al. |
| 6,511,416 B1 * | 1/2003 | Green et al. ............... 600/37 |
| 6,516,216 B1 * | 2/2003 | Fontenot et al. .......... 600/473 |
| 6,591,838 B2 | 7/2003 | Durgin |
| 6,595,909 B2 | 7/2003 | Silverman et al. |
| 6,689,051 B2 | 2/2004 | Nakada et al. |
| 6,908,427 B2 * | 6/2005 | Fleener et al. ............ 600/104 |
| 7,169,115 B2 * | 1/2007 | Nobis et al. ............... 600/567 |

(Continued)

FOREIGN PATENT DOCUMENTS

WO 0235986 5/2002

(Continued)

OTHER PUBLICATIONS

Pentax® EG-2770K and EG-2970K Video Upper G.I. Scope specifications, 70K Series Video Endoscope System, Pentax Corporation, date unknown, 2 pages.

(Continued)

*Primary Examiner*—Linda C Dvorak
*Assistant Examiner*—Alireza Nia
(74) *Attorney, Agent, or Firm*—Shumaker & Sieffert, P.A.

(57) ABSTRACT

The disclosure describes an endoscopic delivery system that includes an endoscope and a tissue-receiving member. The tissue-receiving member includes an opening to receive the distal end of the endoscope. The tissue-receiving member also defines a tissue-receiving space that receives tissue when vacuum pressure is applied to the space through the endoscope. A tool and/or material may be delivered to the tissue drawn into the tissue-receiving space. The tissue-receiving member may be cap-like, and only receive the distal end of the endoscope, or include an overtube that receives a substantial portion of the endoscope. The system may be used to, for example, deliver tissue bulking devices to a location proximate to the lower esophageal sphincter (LES) for treatment of gastroesophageal reflux disease (GERD).

37 Claims, 11 Drawing Sheets

U.S. PATENT DOCUMENTS

| | | |
|---|---|---|
| 2002/0035311 A1 | 3/2002 | Ouchi |
| 2002/0072757 A1 | 6/2002 | Ahmed et al. |
| 2003/0171760 A1 | 9/2003 | Gambale |
| 2003/0187464 A1 | 10/2003 | Tolkoff |
| 2003/0188755 A1 | 10/2003 | Milbocker |
| 2003/0208209 A1 | 11/2003 | Gambale et al. |
| 2004/0009224 A1 | 1/2004 | Miller |
| 2004/0019388 A1* | 1/2004 | Starkebaum ............ 623/23.65 |
| 2004/0034278 A1 | 2/2004 | Adams |
| 2004/0034369 A1 | 2/2004 | Sauer et al. |
| 2004/0037865 A1 | 2/2004 | Miller |
| 2004/0088023 A1 | 5/2004 | Imran et al. |
| 2004/0102804 A1 | 5/2004 | Chin |
| 2004/0138531 A1* | 7/2004 | Bonner et al. ............... 600/156 |
| 2004/0138682 A1 | 7/2004 | Onuki et al. |
| 2004/0158125 A1 | 8/2004 | Aznoian et al. |

FOREIGN PATENT DOCUMENTS

| | | |
|---|---|---|
| WO | WO 2004/021865 | 3/2004 |
| WO | WO 2004/021873 | 3/2004 |

OTHER PUBLICATIONS

Olympus® GIF XP260 and GIF XQ260 Scope specifications, Olympus Corporation, date unknown, 2 pages.

* cited by examiner

DISTAL PORTION OF AN ENDOSCOPIC DELIVERY SYSTEM

FIELD OF THE INVENTION

The invention relates to endoscopes and, more particularly, to endoscopic delivery systems.

BACKGROUND

In addition to allowing a physician to view the interior of a patient, endoscopes are used to deliver a variety of therapies to patients. For example, endoscopes may be used to deliver surgical tools to a selected treatment site. The surgical tools can be used to, for example, ablate or resect tissue at the treatment site. In some cases, vacuum pressure may be used to "grasp" or stabilize selected tissue for treatment. For example, U.S. Pat. No. 6,689,051 to Nakada et al. describes an endoscope hood, into which a high frequency snare is inserted for resection of mucous membrane drawn into the hood by application of vacuum pressure.

Endoscopes may also be used to deliver a fluid or solid material to a treatment site. Again, vacuum pressure may be used to "grasp" or stabilize the tissue that has been selected for receipt of the material. For example, endoscopes may be used to deliver pharmaceuticals to a treatment site. As other examples, endoscopes may be used for delivery of sutures or ligating bands, as described in U.S. Published Application No. 2004/0158125 by Aznoian et al., or an active medical, as described in U.S. Published Application No. 2004/0088023 by Imran et al.

Further, endoscopes may be used to implant bulking devices within a luminal wall within a patient to alter the function of the luminal wall. For example, endoscopes may be used to implant bulking devices proximate to the lower esophageal sphincter (LES) of a patient to treat gastroesophageal reflux disease (GERD). When implanted proximate to the LES, the bulking devices treat GERD by cooperating with the LES to increase the closing pressure of the LES, thereby reducing the likelihood of reflux flow of fluid from the stomach into the esophagus. As other examples, endoscopes may be used to implant bulking devices near the pyloric sphincter or within the fundus of the stomach to treat obesity, or proximate to a urethral or anal sphincter to treat incontinence.

U.S. Published Application No. 2004/0037865 to Miller describes endoscopic delivery of a bio-compatible bulking or stiffening material into the pyloric sphincter area of the stomach. As another example, U.S. Published Application No. 2003/0188755 to Milbocker describes endoscopic delivery of an implantable polymer to the LES. Further, U.S. Pat. No. 6,338,345 to Johnson et al. ('345 patent) describes a system for endoscopically delivering a bulking device to submucosal tissue within a body lumen that includes an endoscope and one of an overtube or a cap-like device that receives the endoscope. A distal end of the overtube or the cap-like device as described in the '345 patent includes a cavity that receives the tissue into which the bulking device will be implanted when vacuum pressure is applied to the cavity via an endoscope.

Table 1 below lists documents that disclose endoscopic delivery systems.

TABLE 1

| Patent Number | Inventors | Title |
|---|---|---|
| 2004/0158125 | Aznoian et al. | Integrated endoscope and accessory treatment device |
| 2004/0138682 | Onuki et al. | Endoscopic suture apparatus |
| 2004/0102804 | Chin | Apparatus and methods for endoscopic surgical procedures |
| 2004/0088023 | Imran et al. | Gastric treatment and diagnosis device and method |
| 2004/0037865 | Miller | Obesity controlling method |
| 2004/0034369 | Sauer et al. | System for endoscopic suturing |
| 2004/0034278 | Adams | Endoscopic resection devices and related methods of use |
| 2004/0019388 | Starkebaum | Methods and implants for retarding stomach emptying to treat eating disorders |
| 2004/0009224 | Miller | Obesity controlling method |
| 2003/0208209 | Gambale et al. | Endoscopic tissue apposition device with multiple suction ports |
| 2003/0187464 | Tolkoff | Distal end for ligating band dispenser |
| 2003/0171760 | Gambale | Tissue capturing and suturing device and method |
| 2002/0072757 | Munir | Ligating band delivery apparatus |
| 2002/0035311 | Ouchi | Tip portion of an endoscope |
| 6,689,051 | Nakada et al. | Endoscope hood for mucous membrane resection |
| 6,595,909 | Silverman et al. | Method for treating tissue with an implant |
| 6,591,838 | Durgin | Implant system and method for bulking tissue |
| 6,338,345 | Johnson et al. | Submucosal prosthesis delivery device |
| RE36,629 | Zaslavsky, et al. | Multiple ligating band dispenser |
| 5,8534164 | Tolkoff | Distal end for ligating band dispenser |
| WO2004021873 | Gambale et al. | Integrated endoscope and accessory treatment device |
| WO2004021865 | Zirps et al. | Endoscopic band ligator |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, at least some of the devices and methods disclosed in the patents of Table 1 may be modified advantageously by following the teachings of the present invention.

SUMMARY OF THE INVENTION

In general, the invention is directed to a tissue-receiving member for use with an endoscope in an endoscopic delivery system, and methods for delivering tools and/or materials using such a system. The tissue-receiving member includes an opening to receive the distal end of the endoscope. The tissue-receiving member may be cap-like, and only receive the distal end of the endoscope, or include an overtube that receives a substantial portion of the endoscope.

The tissue-receiving member also defines a tissue-receiving space that receives tissue when vacuum pressure is applied to the space through the endoscope. Material may be delivered to the tissue drawn into the tissue-receiving space. The system may be used to, for example, deliver tissue bulking devices to a lumen within a patient. For example, the system may be used to deliver tissue bulking devices to locations proximate to the lower esophageal sphincter (LES) for treatment of gastroesophageal reflux disease (GERD).

Various embodiments of the present invention provide solutions to one or more problems existing in the prior art with respect to endoscopic delivery systems. These problems include the potential difficulty or patient discomfort associated with advancing an endoscope, or endoscope and overtube, to certain locations within a patient. Typically, the distal end of endoscopic delivery systems are as large as the endoscope or overtube. Consequently, the full length of a body lumen, including the portion that includes the target location to which the endoscope is advanced, must accommodate the size of the endoscope or overtube. Further, the lumen must accommodate the full size of endoscope or overtube immediately as the endoscope or overtube is introduced into the lumen and advanced.

As a further problem, in existing endoscopic delivery systems that use vacuum pressure to grasp or secure selected tissue, it may be difficult to determine whether the tissue has been adequately grasped or secured. Further, some existing endoscopic delivery systems require that an adequate amount of tissue be grasped or secured for proper placement of a material within tissue. For example, some existing systems require that an adequate amount of tissue be grasped or secured for implantation of bulking devices at a selected depth within a luminal wall. In such systems, the inability to determine whether an adequate amount of tissue has been adequately grasped or secured may lead to improper placement of the bulking devices.

Further, some existing endoscopic delivery systems include a distal attachment for an endoscope, and deliver tools or material to a target location within a patient through a working channel of the endoscope and the attachment. For example, some existing endoscopic delivery systems include a distal attachment for receiving and securing tissue under vacuum pressure that the tools or material will be delivered. In such systems, the working channel and a path through the distal attachment must be aligned so that the tools or materials can pass through the distal attachment. Hence, in such systems, the distal attachment must be attached to the endoscope with a particular rotational alignment so that the working channel and the path are aligned, or the endoscope must be of a type where the working channel is located in the center of the endoscope so that the working channel and the path may be aligned independently of the rotational alignment of the attachment and the endoscope.

Various embodiments of the present invention are capable of solving at least one of the foregoing problems. For example, when embodied in a tissue-receiving member used with an endoscope in endoscopic delivery system, the invention may include features that facilitate easier and more comfortable advancement of the tissue-receiving member and endoscope into a lumen when compared to existing systems. The tissue-receiving member may also include features to facilitate verification of adequate capture of tissue within a tissue-receiving space of the tissue-receiving member. Further, the tissue-receiving member may include features to facilitate advancement of tools and/or material from a working channel of an endoscope through a delivery port of the tissue-receiving member substantially without regard to the rotational orientation of the tissue-receiving member relative to the endoscope or the position of the working channel within the endoscope.

In some embodiments, for example, the distal portion of the tissue-receiving member, which is the distal portion of the system, is smaller than the endoscope. More particularly, a depth of the distal portion may be less than a diameter of the endoscope. The depth of the distal portion may be less than approximately 65 percent of the diameter of the endoscope, within a range from approximately 4 millimeters to approximately 8 millimeters. These features of the tissue-receiving member may facilitate easier and more comfortable advancement of the tissue-receiving member and endoscope into a lumen.

In some embodiments, the tissue-receiving member is formed with a plurality of vacuum apertures, and the endoscope applies vacuum pressure to a tissue-receiving space defined by the tissue-receiving member via the vacuum apertures to draw tissue into the tissue receiving space. When an adequate amount of tissue is drawn into the tissue receiving space, portions, referred to as "blebs," of tissue protrude through each of the vacuum apertures. The blebs may be viewed via the endoscope.

The vacuum apertures may be arranged in a non-axial pattern such that the view of each of the blebs is substantially unobstructed by other blebs. Additionally or alternatively, a surface in which the vacuum apertures are formed may be oriented at a nonzero angle relative to the major axis of the endoscope, e.g., have an upwards slope from the endoscope, such that the view of each of the blebs is substantially unobstructed by other blebs. The angle may be greater than 1 degree. These features of the tissue-receiving member may facilitate verification of adequate capture of tissue within the tissue-receiving space through unobstructed visualization of all of the blebs.

Further, in some embodiments, the tissue-receiving member includes a substantially conical passageway from the distal end of the endoscope to a delivery port. A tool and/or a material may be delivered from a working channel of the endoscope to the tissue received by the tissue-receiving space via the passageway and the delivery port. Where the working channel and delivery port are not aligned, the substantially conical passageway may guide the tool or material into the delivery port as it is advanced. In some embodiments, a diameter of a proximal portion of the passageway is substantially equal to the diameter of the endoscope, so as to capture and guide tools and/or material from a working channel located anywhere within the endoscope. These features of the tissue-receiving member may facilitate advancement of tools and/or material from a working channel of an endoscope through a delivery port of the tissue-receiving member substantially without regard to the rotational orientation of the tissue-receiving member relative to the endoscope or the position of the working channel within the endoscope.

In accordance with the invention, a tissue-receiving member includes a first portion that defines an opening to receive a distal end of an endoscope, and a second portion that extends axially relative to a major axis of the endoscope from a distal end of the first portion to a distal end of the tissue-receiving member. A distal surface of the first portion and an inner surface of the second portion define a tissue-receiving space that receives tissue of a patient when vacuum pressure is applied to the tissue-receiving space via the endoscope. The inner surface of the second portion may be concave in at least a transverse direction, and taper towards its distal end. The distal end of the second portion may define an opening to the tissue-receiving space, or may be closed by a wall such that the tissue-receiving space is a cavity that is substantially closed on three sides.

In some embodiments, a depth of the second portion in a transverse direction relative to the major axis of the endoscope is less than a diameter of the endoscope along substantially the entire length of the second portion. The depth of the second portion may be less than approximately 65 percent of the diameter of the endoscope. The diameter of the endoscope may be within a range from approximately 8 millimeters to approximately 12 millimeters, and the depth of the second portion is within a range from approximately 4 millimeters to approximately 8 millimeters.

The inner surface of the second portion is formed with a plurality of vacuum apertures for application of vacuum pressure from the endoscope to the tissue-receiving space. In some embodiments, the vacuum apertures are arranged in a non-axial pattern, or the inner surface of the second portion may be oriented at nonzero angle relative to the major axis of the endoscope, either or both of which may allow unobstructed viewing of tissue blebs protruding through the vacuum apertures via the endoscope. The angle at which the inner surface of the second portion is oriented may be greater than approximately 1 degree. In some embodiments, a distal surface of the first portion may also be formed with one or more vacuum aperture for application of vacuum pressure from the endoscope to the tissue-receiving space. Vacuum apertures located on the distal surface of the first portion in addition to the inner surface of the second portion may increase the ability of the tissue-receiving member to draw tissue into the tissue-receiving space.

In some embodiments, the tissue-receiving member is formed with a delivery port through the distal surface of the first portion to allow delivery of tools and/or materials from a working channel of the endoscope to tissue received within the tissue-receiving space. The tissue-receiving member may also be formed with a substantially conical passageway from the distal end of the endoscope to the delivery port, which may guide the tools or material from a working channel of the endoscope to the delivery port without regard for the alignment of the working channel and the delivery port. The diameter of a proximal portion of the conical passageway may be substantially equal to the diameter of the endoscope, and the wall of the substantially conical passageway may be substantially transparent to, for example, allow endoscopic visualization through the wall of tissue blebs protruding through vacuum apertures of the first and second portions. The wall of the substantially conical passageway and/or the delivery port may also include one or more vacuum apertures, so that vacuum pressure may be applied from the endoscope to the tissue-receiving space via the apertures of the passageway or port, and the apertures of the surfaces of the first and second portions.

As indicated above, the tissue-receiving member may be cap-like and only receive the distal end of the endoscope, e.g., a proximal end of the first portion is located within a patient when the endoscope is advanced into the patient. Alternatively, the tissue-receiving member may include an overtube that receives a substantial portion of the endoscope, and whose proximal end is located outside of the patient when the endoscope is advanced into the patient. The overtube may include lumen in addition to or as an alternative to those provided by the endoscope, such as an additional or alternative working channel or vacuum lumen.

In some embodiments, the invention comprises an endoscopic delivery system including an endoscope and any of the tissue-receiving member embodiments described above, or a method for using such a system. In exemplary embodiments, a clinician may use such a system to endoscopically deliver a bulking device to a lumen of a patient. For example, the tissue-receiving member and endoscope may be used to endoscopically deliver bulking device to a location proximate to a lower esophageal sphincter (LES) of the patient for treatment of gastroesophageal reflux disease (GERD). In such embodiments, the clinician applies vacuum pressure to the tissue-receiving space defined by the tissue-receiving member via the endoscope to draw tissue of the lumen into the tissue-receiving space, and advances a bulking device into the tissue drawn into the tissue-receiving space. More particularly, the clinician may advance the bulking device through a working channel of the endoscope, a substantially conical passageway within the tissue-receiving member, and a delivery port of the tissue-receiving member, and into the tissue. As indicated above, a diameter of a proximal portion of the passageway may be substantially equal to the diameter of the endoscope to enable the bulking device to be guided to the delivery port by the substantially conical passageway.

As indicated above, the endoscope may apply vacuum pressure to the tissue-receiving space via a plurality vacuum apertures through an inner surface of the tissue-receiving member, and the apertures may be arranged in a non-axial pattern. Further, a wall of the substantially conical passageway may substantially transparent. Through the endoscope and the wall, the clinician may visualize a respective tissue bleb protruding through each of the plurality of vacuum apertures to confirm adequate capture of tissue prior to advancing the bulking device through the delivery port.

In some embodiments, the clinician may first advance a needle through the working channel, the substantially conical passageway, and the delivery port, and into the tissue drawn into the tissue-receiving space to form the hole in tissue. The clinician may then advance the bulking device into the tissue through the hole. Further, in some embodiments, the clinician injects a fluid via the needle to create an implantation pocket within the tissue, and advances the bulking device into the implantation pocket through the hole. When adequate tissue is captured within the tissue-receiving space, the depth of the tissue-receiving space may control the depth within the luminal wall at which the bulking device is implanted. In exemplary embodiments, the bulking device is advanced into a submucosal layer of the luminal wall.

In comparison to known endoscopic delivery systems, various embodiments of the invention may provide one or more advantages. For example, as described above, the invention may facilitate easier and more comfortable advancement of the system into a lumen when compared to existing systems, visual verification of adequate capture of tissue by an endoscope attachment, and advancement of tools and/or material from a working channel of an endoscope through an endoscope attachment substantially without regard to the rotational orientation of the attachment relative to the endoscope or the position of the working channel within the endoscope.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

Figure 1:
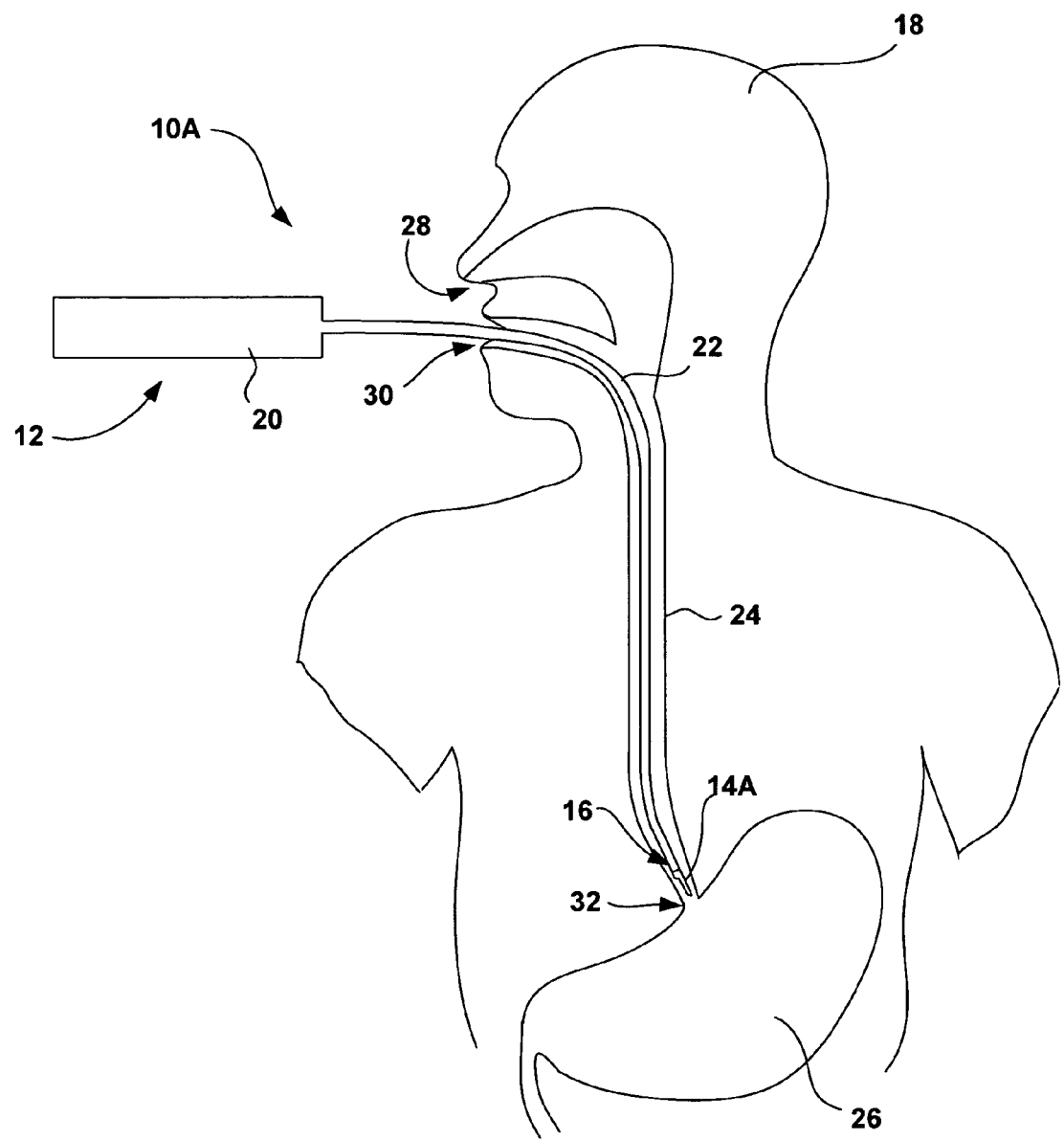
FIG. 1 is a conceptual diagram illustrating an example endoscopic delivery system that includes an endoscope and a tissue-receiving member.

FIG. 1 is a conceptual diagram illustrating an example endoscopic delivery system 10A that includes an endoscope 12 and a tissue-receiving member 14A that is located at the distal end 16 of endoscope 12. As will be described in greater detail below, a user of system 10, e.g., a physician, may deliver tools and/or materials to selected tissue of a patient 18 through endoscope 12 and tissue-receiving member 14A. In embodiments in which the user delivers a tool to the tissue, tissue-receiving member 14A may facilitate "grasping" or stabilization of the selected tissue while it is worked on by the tool, e.g., grasping or stabilization of a selected amount of the tissue to be worked on by the tool. In embodiments in which the user delivers material to the tissue, tissue-receiving member 14A may additionally facilitate delivery of the material at a selected depth within the tissue.

Further, as will be described in greater detail below, tissue-receiving member 14A may include features that provide one or more advantages in comparison with known endoscopic delivery systems. For example, tissue-receiving member 14A may include features that facilitate easier and more comfortable advancement of system 10A into a lumen of patient 18 when compared to existing systems. As another example, tissue-receiving member 14A may include features that facilitate visual verification of adequate capture of selected tissue by the tissue-receiving member, i.e., determination of whether the tissue is adequately stabilized, or Whether an adequate amount of tissue has been captured for delivery of a material to a selected depth within the tissue. Additionally, tissue-receiving member 14A may include features that facilitate advancement of tools and/or material from a working channel of endoscope 12 through the tissue-receiving member substantially without regard to the rotational orientation of the tissue-receiving member relative to the endoscope or the position of the working channel within the endoscope.

Endoscope 12 includes a proximal portion, referred to herein as a handle 20, and a flexible probe 22 that extends from handle 20. In general, a user manipulates handle 20, which remains outside of patient 18, to guide distal end 16 of flexible probe 22 and tissue-receiving member 14A through a lumen of the patient to target tissue. For example, in FIG. 1, endoscopic delivery system 10A is shown in conjunction with an esophagus 24 and stomach 26 of patient 18, and distal end 16 of flexible probe 22 and tissue-receiving member 14A are shown extending into the lumen defined by esophagus 24 and toward stomach 26. Distal end 16 of flexible probe 22 and tissue-receiving member 14A enter esophagus 24 via either nasal cavity 28 or oral cavity 30.

In some embodiments, endoscopic delivery system 10A may deliver tissue bulking devices to the target tissue captured by tissue-receiving member 14A, such as tissue proximate to LES 32. In such embodiments, tissue-receiving member 14A may facilitate "grasping" or stabilization of the target tissue, and delivery of the bulking devices at a selected depth within the tissue. For example, bulking devices may be delivered to a submucosal layer of a luminal wall of patient 18, such as esophagus 24 or stomach 26. Upon implantation of a bulking device, endoscopic delivery device 44 may be repositioned to grasp other target tissues and deliver another bulking device 14.

Figure 2A:
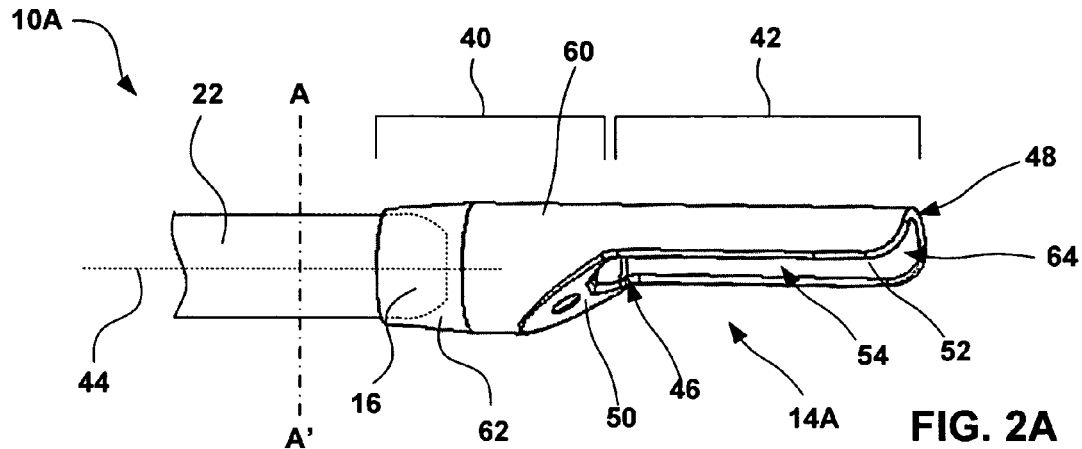
FIGS. 2A and 2B are perspective and side-view diagrams, respectively, further illustrating the distal portion of the endoscopic delivery system of FIG. 1.
Figure 2B:
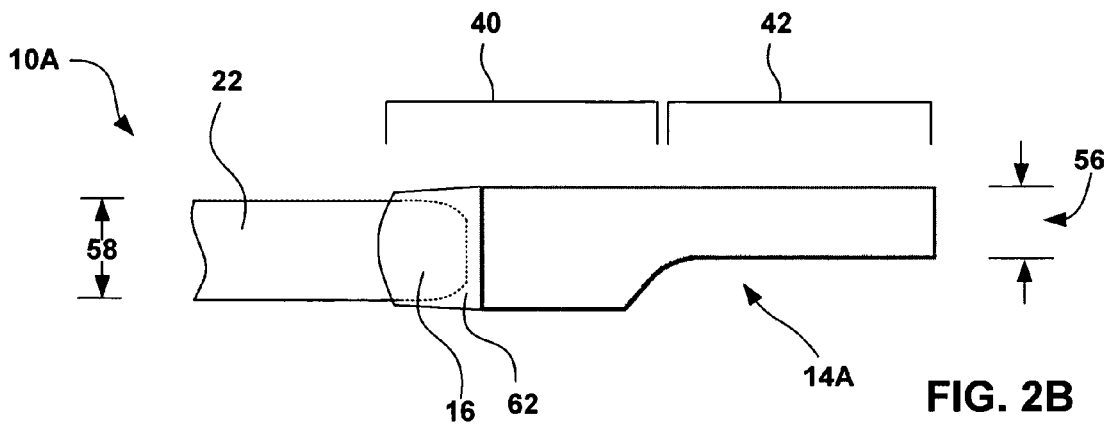

FIGS. 2A and 2B are perspective and side diagrams, respectively, further illustrating the distal portion of endoscopic delivery system 10A, including distal end 16 of flexible probe 22 and tissue-receiving member 14A. As illustrated in FIGS. 2A and 2B, tissue-receiving member 14A includes a first portion 40 that receives distal end 16 of flexible probe 22, i.e., the distal end of endoscope 12, and a second portion 42 that extends axially relative to a major axis 44 of endoscope 12 from a distal end 46 of first portion 40 to a distal end 48 of tissue-receiving member 14A, which is the distal end of endoscopic delivery system 10A. A distal surface 50 of first portion 40 and an inner surface 52 of second portion 42 define a tissue-receiving space 54 that receives tissue of patient 18 when vacuum pressure is applied to the tissue-receiving space via endoscope 12. As illustrated in FIG. 2A, in some embodiments, major axis 44 of endoscope may be substantially the same as the longitudinal axis of a distal portion of endoscope 22, such as, e.g., the longitudinal axis of the distal end 16 of endoscope 22.

Distal surface 50 of first portion 40 may be angled relative to a transverse axis of endoscope 12, which is coincident with line A-A' shown in FIG. 2A. Further, inner surface 52 of second portion 42 may be concave in at least the transverse direction, and tapered towards distal end 48. These shapes of surfaces 50, 52 may provide an overall shape of the distal portion of endoscopic delivery system 10 that is generally atraumatic when the distal portion is introduced into a lumen of patient 18, such as esophagus 24. Further, the shapes of surfaces 50, 52 may enable capture and retention of selected tissue within tissue-receiving space 54.

However, these shapes are merely exemplary, and surfaces 50, 52 may have any shape or orientation relative to the axes of endoscope 12. For example, distal surface 50 may be parallel to the transverse axis of endoscope 12. Further, inner surface 52 may be concave in multiple directions, provide a smooth, curved surface, be box or trench-like with multiple sub-surfaces oriented at angles with each other, or be flat.

In some embodiments, a depth 56 of second portion 42 in a transverse direction relative to major axis 44 of endoscope 12, and along substantially the entire length of the second portion, is less than a diameter 58 of endoscope 12. Depth 56 may be less than approximately 65 percent of diameter 58, less than approximately 50 percent of diameter 58, or, more preferably, less than approximately 40 percent of diameter 58. As an example, diameter 58 may be within a range from approximately 8 millimeters to 12 millimeters, and depth 56 may be within a range from approximately 4 millimeters to approximately 8 millimeters. The distal portion of system 10 may be smaller by virtue of depth 56 being less than diameter 58, thereby facilitating easier and more comfortable advancement of system 10 into a lumen of patient 18, such as esophagus 24. The dimensions of first portion 40 may be substantially similar to diameter 48, and the length of tissue-receiving member may be within a range from approximately 35 millimeters to approximately 55 millimeters.

Tissue-receiving member 14A may be made of any one or more of a variety of materials. For example, tissue-receiving member 14A may include biocompatible metals or polymers that are resilient to deformation under vacuum pressure, such as such as polycarbonate, acrylic, high-density polyethylene (HDPE), nylon, polytetrafluorethylene (PTFE), stainless steel, or titanium. Tissue-receiving member 14A may also include biocompatible materials to provide a more pliable and atraumatic surface, e.g., a silicone coating. A silicone gel coating, for example may also provide more "tacky" surfaces for the tissue-receiving member, which may aid in retention of tissue within tissue-receiving space 54.

Tissue-receiving member 14A may be formed from a single component, or multiple components. In some embodiments, tissue-receiving member 14A includes a main body 60, and a separate endoscope engagement member 62. Engagement member 62 may define an opening that receives distal end 16 of flexible member 22. Engagement member 62 may include mechanical features for engaging the endoscope, e.g., corresponding features on the endoscope, or be sized and formed with materials such that it retains the endoscope through a friction engagement with the endoscope. Both main body 60 and endoscope engagement member 62 may be formed of one or more of the materials identified above, and may be attached to each other using any type of mechanical, welded, or adhesive connection.

Further, the components of tissue-receiving member 14A may be formed using any of a variety of processes, such as molding, casting, or deposition processes. The edges of tissue-receiving member may be rounded to provide atraumatic surfaces for easier and more comfortable introduction of system 10 into patient 18. In the illustrated example, second portion 42 of tissue-receiving member 14A defines an opening 64 at distal end 48. Allowing distal end 48 to include opening 64 may allow tissue receiving member 14A to more easily be formed by molding processes.

Figure 3:
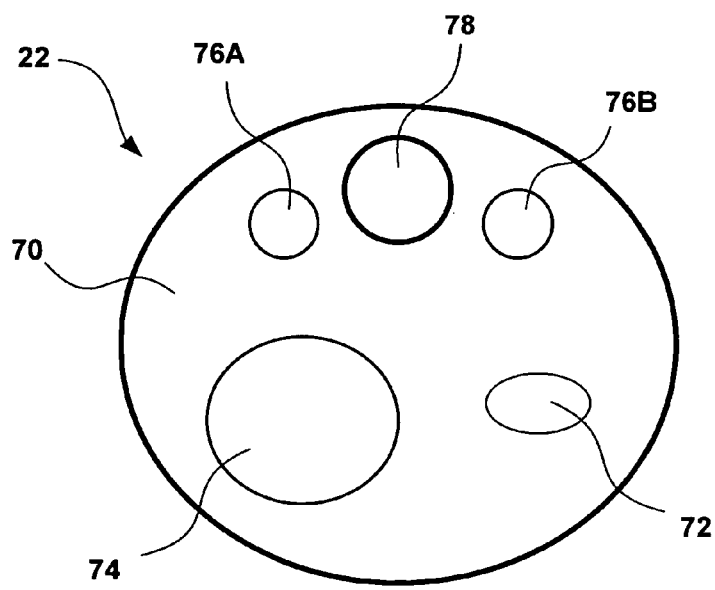
FIG. 3 is cross-sectional diagram further illustrating the endoscope of FIGS. 1 and 2, the cross-section taken along line A-A' of FIG. 2.

FIG. 3 is a cross-sectional diagram further illustrating flexible probe 22 of endoscope 12, the cross-section taken along line A-A' of FIG. 2A. Flexible probe 22 includes an elongated main body 70, which may have a substantially round shape in its transverse cross-section, as shown in FIG. 3. Main body 70 may be formed of any one or more of a variety of biocompatible polymers, such as such as polycarbonate, acrylic, HDPE, nylon, or PTFE, and may include a silicone coating to provide an atraumatic surface.

In some embodiments, main body 70 may be formed to be flexible in transverse directions and more resilient in the axial direction, to facilitate advancement of flexible probe 22 through a lumen of patient 18 while allowing deflection of distal end 16 of flexible probe 22 and tissue-receiving member 14A. Main body 70 may include one or more wires or cables (not shown) that extend from locations proximate to distal end 16 to handle 20 of endoscope 12, and a user may manipulate the cables or wires via the handle 20 to deflect distal end 16 and thereby guide tissue-receiving member 14A to the tissue selected to receive tools and/or materials. Main body 70 may include features, such as detents or the like, that interact with corresponding features of endoscope engagement member 62 of tissue-receiving member 14A.

As shown in FIG. 3, main body 70 defines a vacuum lumen 72 that extends from distal end 16 to handle 20, which may include a vacuum port (not shown) to enable application of vacuum pressure to lumen 72. Lumen 72 may, in turn, apply vacuum pressure to tissue-receiving member 14A, to enable tissue to be drawn into tissue-receiving space 54. Main body 70 also defines a working channel 74 that extends from distal end 16 to handle 20, which may include a port to allow a user to advance tools and/or materials through working channel 74 to distal end 16 of flexible probe 22. Further, main body 70 includes light guides 76A and 76B (collectively "light guides 76") and a lens 78 that extend from distal end 16 to handle 20, where they may interface with light source and monitor, and thereby allow a user to view objects located at distal end 16 and within the field of vision of lens 78. Alternatively, endoscope 12 may accomplish visualization by a video chip located at the distal tip of flexible probe, which is coupled to a wire that traverses through main body to a proximal end of the endoscope. Endoscope 12 may correspond to any of a variety of commercially available endoscopes, such endoscopes bearing model numbers EG-2770K or EG-2770K, which are commercially available from Pentax Imaging Co., or endoscopes bearing model numbers GIF-XQ260 or GIF-XP260, which are commercially available from Olympus Inc.

Figure 4A:
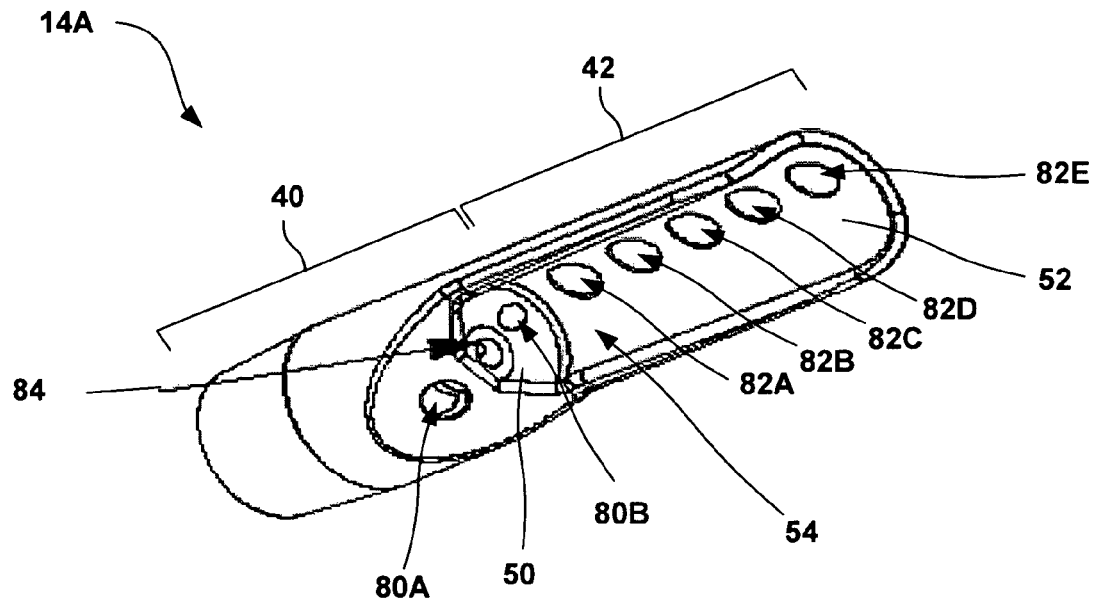
FIGS. 4A and 4B are perspective and bottom-view diagrams, respectively, further illustrating the tissue-receiving member of FIGS. 1 and 2.
Figure 4B:
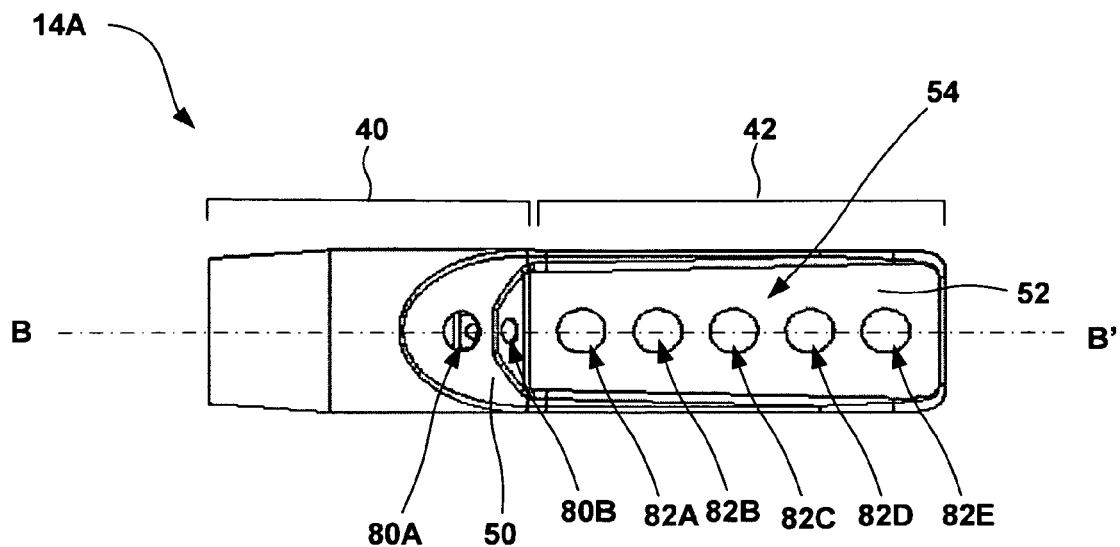

FIGS. 4A and 4B are perspective and bottom-view diagrams, respectively, further illustrating tissue-receiving member 14A. In particular, FIGS. 4A and 4B illustrate vacuum apertures 80A and 80B (collectively "vacuum apertures 80") formed in distal surface 50 of first portion 40, and vacuum apertures 82A-82E (collectively "vacuum apertures 82") formed in inner surface 52 of second portion 42. FIGS. 4A and 4B also illustrates a delivery port 84 formed through the distal surface of the first portion.

Vacuum lumen 72 of flexible probe 22 (FIG. 3) applies vacuum pressure to tissue-receiving space 54 through apertures 80, 82 to draw selected tissue of patient 18 into the tissue-receiving space. Vacuum pressure applied through vacuum apertures 80 located on distal surface 50 may draw tissue toward inner surface 52, and vacuum pressure applied through vacuum apertures 82 located on inner surface 52 may fully draw a selected amount of tissue into the tissue-receiving space, and retain the tissue within the tissue-receiving space. In each aspect, the tissue-receiving member may be configured to transmit vacuum pressure received from a vacuum source through a vacuum port and vacuum lumen 72 of endoscope 12 to tissue receiving space 54 via vacuum apertures 80 and/or vacuum apertures 82 when the endoscope 12 is received in the opening of engagement member 62 (FIGS. 2A and 2B). A user may deliver tools and/or materials to the selected tissue via working channel 74 of flexible probe 22 (FIG. 3) and delivery port 84. As shown in FIG. 4A, for example, delivery port 84 may be formed in distal surface 50 substantially between inner surface 52 and vacuum aperture 80A.

Figure 5A:
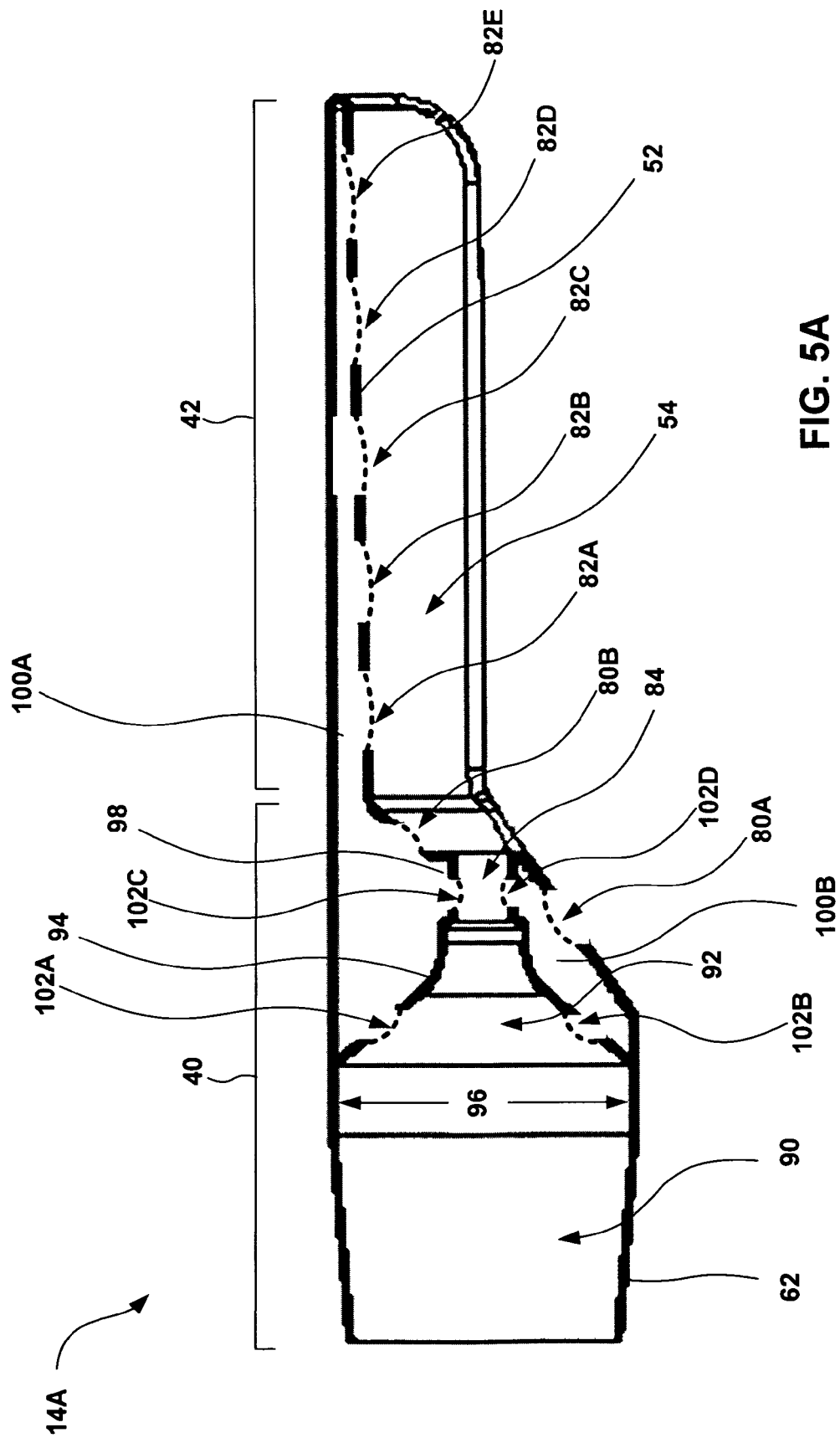
FIGS. 5A and 5B are cross-sectional diagrams further illustrating the tissue-receiving member of FIGS. 1, 2, 4A and 4B, the cross-section taken along line B-B' of FIG. 4B.
Figure 5B:
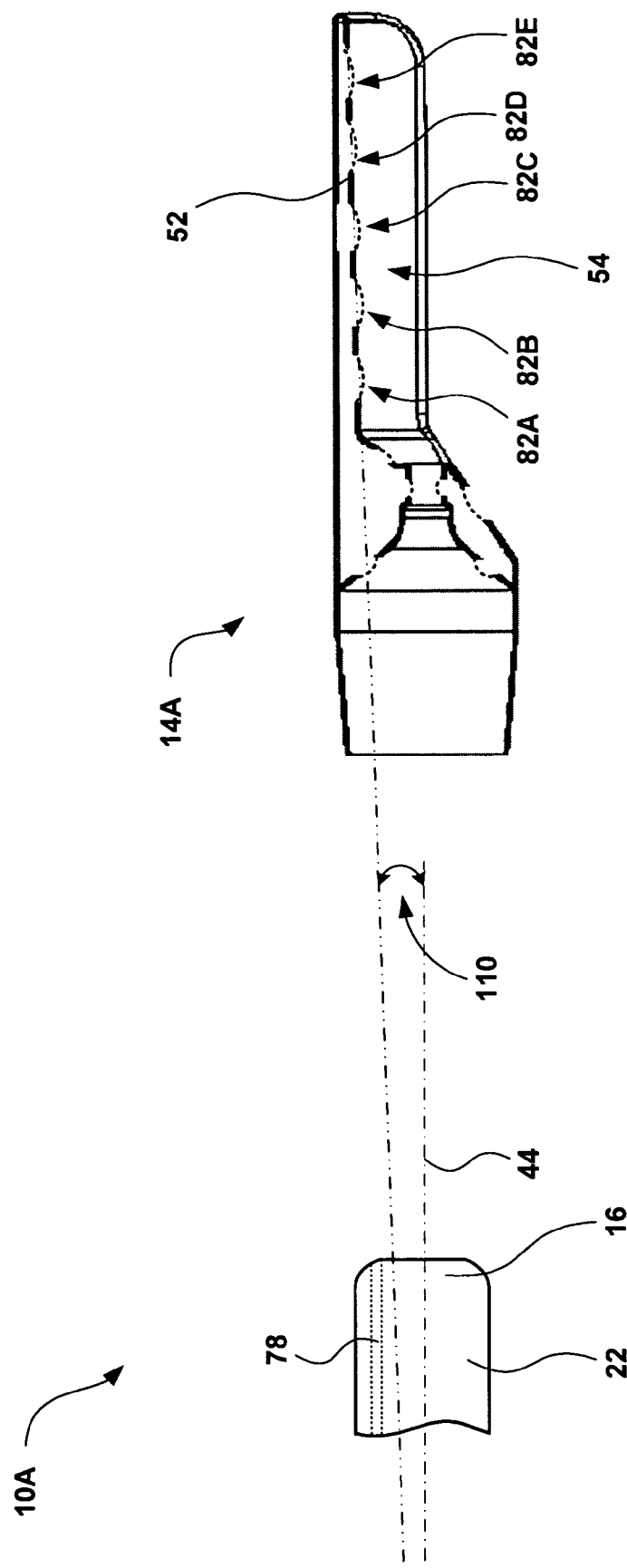

Although illustrated in FIGS. 4A and 4B as having a substantially round shape, vacuum apertures 80, 82 may have any shape, such as any ellipsoid, rectangular, geometric or irregular shape. In the illustrated embodiment, vacuum apertures 82 are arranged in an axial pattern, e.g., along major axis 44 of flexible probe 22, which is coincident with line B-B' of FIG. 4B. However, in other embodiments a tissue-receiving member according to the invention may include apertures 82 through inner surface 52 that are arranged in a non-axial pattern, as will be described in greater detail below FIGS. 5A and 5B are cross-sectional diagrams further illustrating tissue-receiving member 14A, the cross-section taken along line B-B' of FIG. 4B. As illustrated by FIGS. 5A and 5B, endoscope engagement member 62 of first portion 40 defines an opening 90 to receive distal end 16 of flexible probe 22. Engagement member 62 and opening 90 may be substantially annular in their transverse cross-section to receive flexible probe 22, which has a substantially round shape in its transverse cross-section.

First portion 40 also includes a substantially conical passageway 92 from opening 90 to delivery port 84. A user may deliver tools or materials to distal end of flexible probe 22 via working channel 74, through passageway 92 and delivery port 84, and into selected tissue retained by tissue-receiving space 54 when under vacuum pressure. Because passageway 92 is substantially conical, working channel 74 and delivery port 84 need not be aligned along a common axis to facilitate delivery of tools or materials from working channel 74 to delivery port. In other words, a wall 94 of passageway 92 may guide the tool or material from working channel 74 to delivery port 84 without regard for the alignment of the working channel and the delivery port, e.g., without regard to the rotational orientation of tissue-receiving member 14A relative to flexible member 22 or the position of working channel 74 within flexible member 22. The diameter 96 of a proximal portion of passageway 92 may be substantially equal to diameter 58 of flexible probe 22 (FIG. 2B) to allow passageway 92 to guide tools or materials from working channels 74 located substantially anywhere within the cross-section of flexible probe 22 into delivery port 84. As illustrated in FIG. 5A, substantially conical passageway 92 is configured such that the inner diameter of passageway 92 tapers moving from a proximal portion of passageway 92 towards delivery port 84. As a result, in some examples, the diameter 96 of a proximal portion of passageway 92 may be greater than diameter of a distal portion of passageway 92, i.e., the diameter of the portion of passageway proximate to delivery port 84.

One or both of wall 94 of passageway 92, and a wall 98 of delivery port 84 may include vacuum apertures to allow vacuum lumen 72 to apply vacuum pressure through spaces 100A and 100B ("collectively "spaces 100"), apertures 80, 82, and into tissue-receiving space 54. In the illustrated embodiment, walls 94, 98 include apertures 102A-102D, (collectively "apertures 102"). Apertures 102 may have any shape, as described above with reference to apertures 80, 82. Apertures 102 may be angled toward flexible probe 22 when traversing from passageway 92 or port 84 into spaces 100 to avoid presenting a surface that could "catch" or otherwise impede a tool or material delivered though the passageway or port.

When vacuum lumen 74 applies vacuum pressure to tissue-receiving space 54 through apertures 80, 82, portions of the target tissue drawn into the tissue-receiving space may protrude through the apertures. These protrusions are referred to as tissue "blebs." When the target tissue is adequately drawn into tissue-receiving space 54, e.g., the target tissue is adequately stabilized or an adequate amount of the target tissue has been captured, a bleb may protrude through each of apertures 80, 82. Wall 94 of passageway 92 may be substantially transparent to allow user to view tissue blebs protruding through the apertures via lens 98 of endoscope 12.

FIG. 5B illustrates the cross-section of tissue-receiving member 14A in conjunction with distal end 16 of flexible probe 22 of endoscope 12. As illustrated by FIG. 5B, inner surface 52 of second portion 44 of tissue-receiving member 14A may be oriented at nonzero angle 110 relative to major axis 44 of flexible probe 22 in a direction substantially parallel to major axis 44 of the endoscope 12, e.g., have an upwards slope from the flexible probe. Accordingly, as illustrated in FIG. 5B, in some embodiments, the distance between inner surface 52 of second portion 44 and major axis 44 in the direction orthogonal from major axis 44 increases moving distally along major axis 44 along substantially the entire length of inner surface 52. With inner surface 52 oriented at angle 110, a user of system 10A may have an unobstructed view of tissue blebs protruding through each of vacuum apertures 82 through inner surface 52 via lens 78. In other words, angle 110 may facilitate visual verification of adequate capture of tissue within tissue-receiving space 54 through unobstructed visualization of whether blebs protrude through all of apertures 82. Angle 110 may be greater than approximately 1 degree, greater than 2 degrees, or, more preferably, greater than 5 degrees.

Figure 6A:
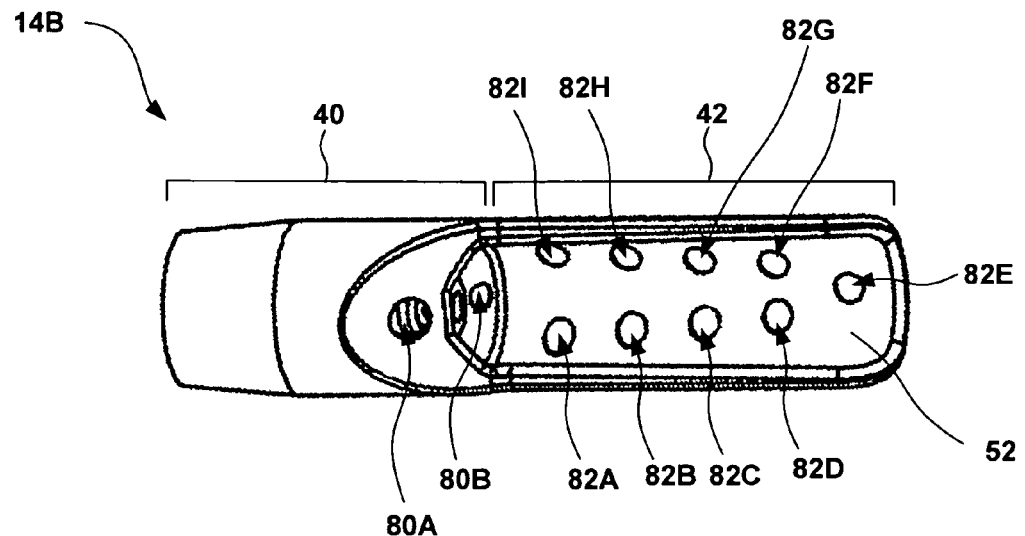
FIGS. 6A and 6B are bottom-view diagrams illustrating other example tissue-receiving members.
Figure 6B:
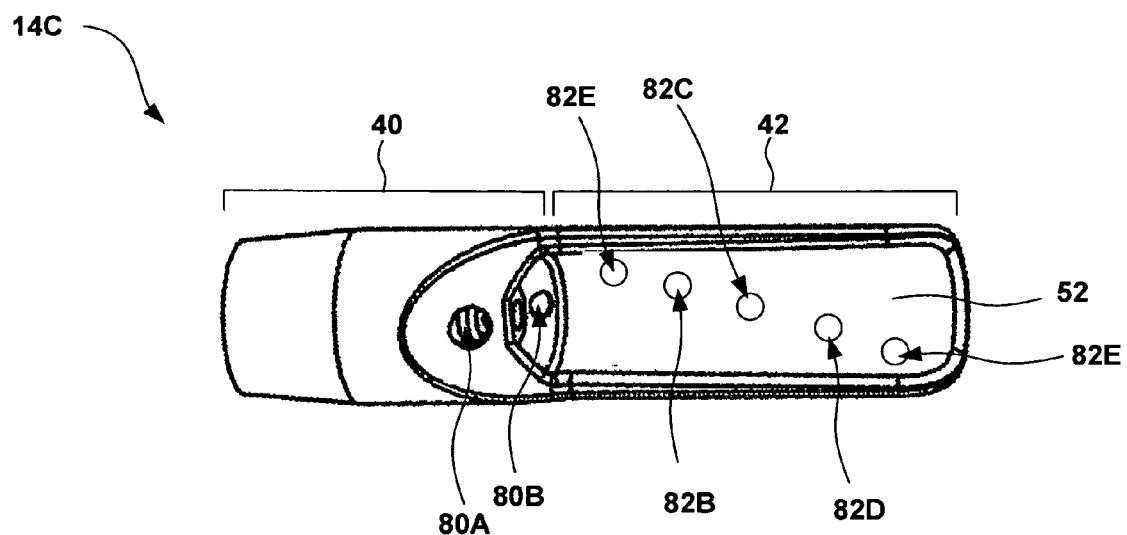

FIGS. 6A and 6B are bottom-view diagrams illustrating other example tissue-receiving members 14B and 14C, respectively. Tissue-receiving members 14B and 14C include vacuum apertures 82A-82I and vacuum apertures 82A-82E (collectively "vacuum apertures 82"), respectively, formed through their respective inner surfaces 52. In contrast to vacuum apertures 82 of tissue-receiving member 14A, vacuum apertures 82 of tissue-receiving members 14B and 14C are arranged in non-axial patterns on the inner surfaces, i.e., are not aligned with axis 44 of flexible probe 22. With apertures 82 arranged in a non-axial pattern, a user of an endoscopic delivery system including one of tissue-receiving members 14B and 14C may have an unobstructed view of tissue blebs protruding through each of vacuum apertures 82 via lens 78, i.e., the blebs may be dispersed throughout a horizontal field of vision provided by lens 78 such that they do not obstruct each other. As shown in FIGS. 6A and 6B, the non-axial arrangement of vacuum apertures 82 is such that [[a]] any straight line bisecting any two of vacuum apertures 82 is nonparallel to axis 44 of flexible probe 22 (FIG. 2A). In some embodiments, the non-axial pattern of vacuum apertures 82 may provide a straight path from lens 78 (FIG. 5B) to a vacuum aperture located at approximately the distal end of second portion 82, e.g., vacuum aperture 82E, that does not intersect at least a portion of vacuum apertures 82 other than that of the vacuum aperture located at approximately the distal end of second portion 82, e.g., vacuum aperture 82E.

Figure 7:
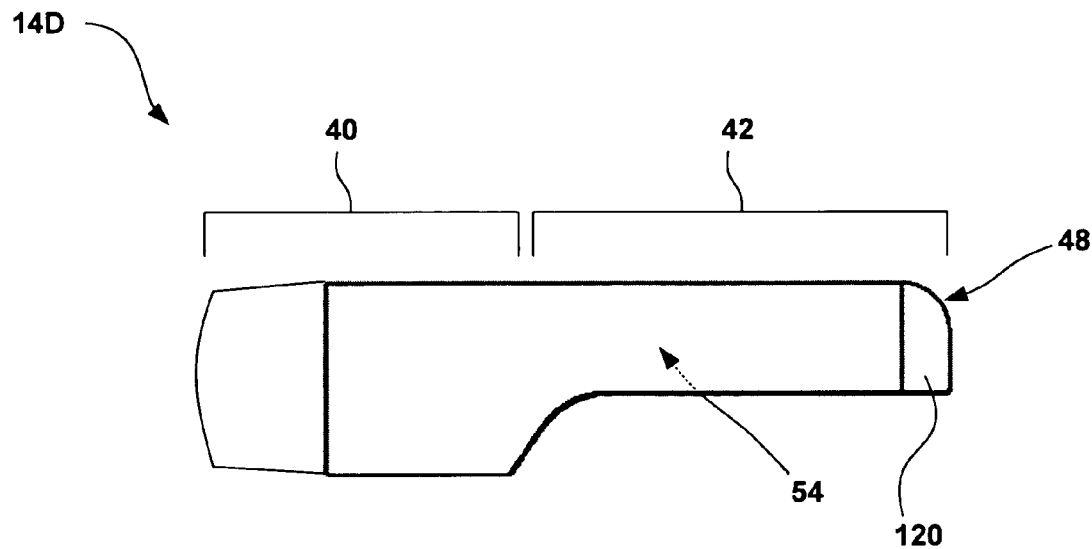
FIG. 7 is a side-view diagram illustrating another example tissue-receiving member.

FIG. 7 is a side-view diagram illustrating another example tissue-receiving member 14D. Second portion 42 of tissue-receiving member 14D includes a wall 120 at distal end 48 that extends substantially perpendicularly from the distal end. With wall 120 located at distal end 48 tissue-receiving member 16D defines a tissue-receiving space 54 that is a cavity that is substantially closed on three sides, which may more easily retain tissue than open-ended embodiments, such as the tissue-receiving spaces 54 defined by tissue-receiving members 14A-14C. Wall 120 may also present an atraumatic surface when tissue-receiving member 14D is advanced through a lumen of patient 18, such as esophagus 24.

Figure 8:
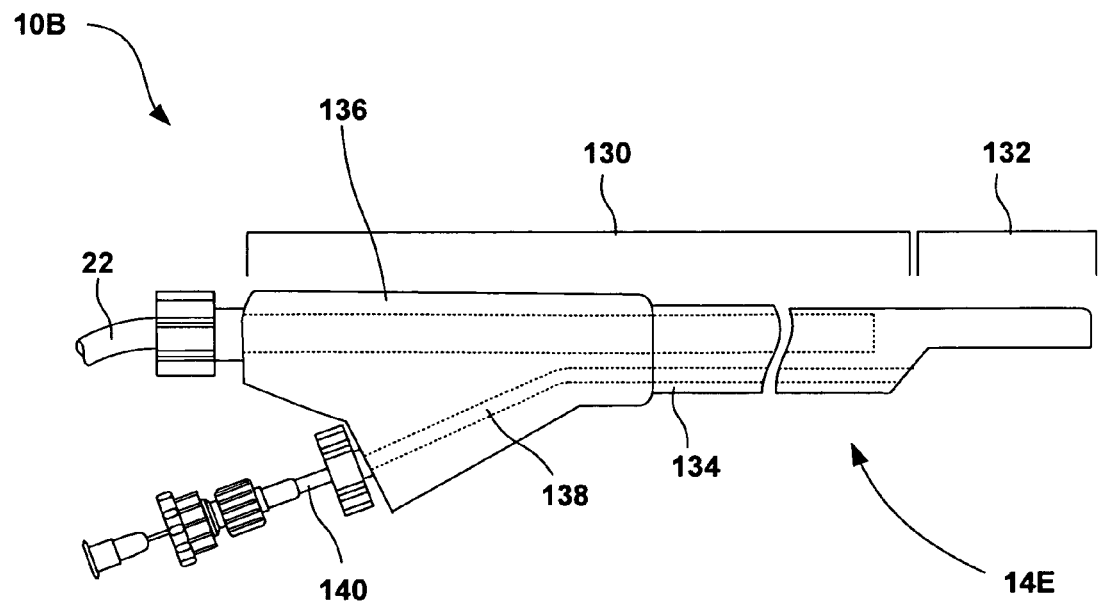
FIG. 8 is a side-view diagram illustrating another example endoscopic delivery system that includes an endoscope and a tissue-receiving member.

FIG. 8 is a side-view diagram illustrating another example endoscopic delivery system 10B that includes an endoscope 12 and a tissue-receiving member 14E. Like tissue-receiving members 14A-14D, tissue-receiving member 14E includes a first portion 130 that defines an opening to receive a distal end of flexible probe 22 of endoscope 12, and a second portion 132 that extends axially relative to a major axis 44 of endoscope 12 from a distal end 46 of first portion 130 to a distal end 48 of tissue-receiving member 14E, which is the distal end of endoscopic delivery system 10B. Also, like tissue-receiving members 14A-14D, a distal surface 50 of first portion 130 and an inner surface 52 of second portion 132 of tissue-receiving member 14E define a tissue-receiving space 54 that receives tissue of patient 18 when vacuum pressure is applied to the tissue-receiving space via endoscope 12.

Additionally, tissue-receiving member 14E may include other features described above with reference to tissue-receiving members 14A-14D. For example, a depth 56 of second portion 132 may be less than a diameter 58 of flexible probe 22 of endoscope 12. Additionally, the inner surface of second portion 132 may be oriented at an angle 110 relative to the major axis 44 of endoscope 12, and may define vacuum apertures 82 that are arranged in a non-axial pattern. Further, tissue-receiving member 14E may include a substantially conical passageway 92, the wall 94 of which may be transparent.

However, unlike tissue-receiving members 14A-D, first portion 130 of tissue-receiving member 14E includes an overtube 134. Overtube 134 receives a substantial portion of flexible probe 22 of endoscope 12, and a proximal portion 136 of overtube 134 remains outside of patient 18 when overtube is advanced into patient 18 to target tissue within the patient. Overtube 134 may be formed of any one or more of the materials, and by any one or more of the processes described above with reference to tissue-receiving members 14A-14D and flexible probe 22. In addition to a lumen to receive flexible probe 22, overtube 134 may provide one or more working channels 138 through which a user may deliver a tool 140 and/or material to tissue received by the tissue-receiving space defined by first and second portions 130, 132. Working channel 138 may be used as an alternative to or in addition to working channel 74 of flexible probe 22.

FIGS. 9A-9E are cross-section side view diagrams illustrating an example technique for delivery of tools and materials to selected tissue using endoscopic delivery system 10A. More particularly, FIGS. 9A-9E illustrate implantation of a tissue bulking device 150 using endoscopic delivery system 10A. For ease of illustration, a number of features of tissue-receiving member 14A and flexible probe 22 described above and illustrated in FIGS. 1-8 are not labeled in FIGS. 9A-9E.

FIGS. 9A-9E depict system 10A implanting bulking device 150 within a luminal wall 152 within patient 18, such as the wall of esophagus 24 or stomach 26 (FIG. 1). More particularly, FIGS. 9A-9E depict system 10A implanting bulking device 150 within a submucosal layer 154 of luminal wall 152, which is between a mucosal layer 156 and a muscular layer 158. However, system 10A may be used to implant bulking devices 150 within or between any layers of luminal wall 150, such as any of the depicted layers 154-158.

In the illustrated embodiments, bulking devices 150 have a predetermined form, i.e., are substantially solid when implanted. In other embodiments, however, bulking devices 150 may be formed by injecting one or more fluid materials into an implant site that solidify in situ to form a bulking device. Bulking devices 150 are illustrated herein as having substantially elliptical, cylindrical, or rod-like shapes with blunt, atraumatic edges. However, bulking devices 150 may have any regular or irregular shape.

Bulking devices 150 may be formed from an expandable material that is initially implanted with a reduced, unexpanded size. Upon implantation, bulking devices 150 expand to a larger size to provide a desired degree of tissue bulking. As an example, bulking devices 150 may formed from a hydrogel material that is implanted in an at least partially dehydrated state having a reduced size. Upon rehydration following implantation, bulking devices 150 assume an expanded state and increased size. Hence, the initial, unexpanded size of bulking devices 150 facilitates implantation, but subsequent expansion provides the desired degree of tissue bulking.

FIG. 9A-9D depict a portion of luminal wall 152 drawn into tissue-receiving space 54 by vacuum pressure applied to the tissue-receiving space. FIGS. 9A-9D also depict tissue blebs 160A-160G (collectively "tissue blebs 160") protruding through apertures 80, 82. As described above, a user of system 10A may view blebs 160 to determine whether tissue of luminal wall 152 is adequately captured by tissue-receiving member 14A. If the user determines that the tissue is not adequately captured, the user may remove vacuum pressure, reposition the tissue-receiving member, reapply vacuum pressure, and view blebs 160 to determine whether the tissue is then adequately captured.

Figure 9A:
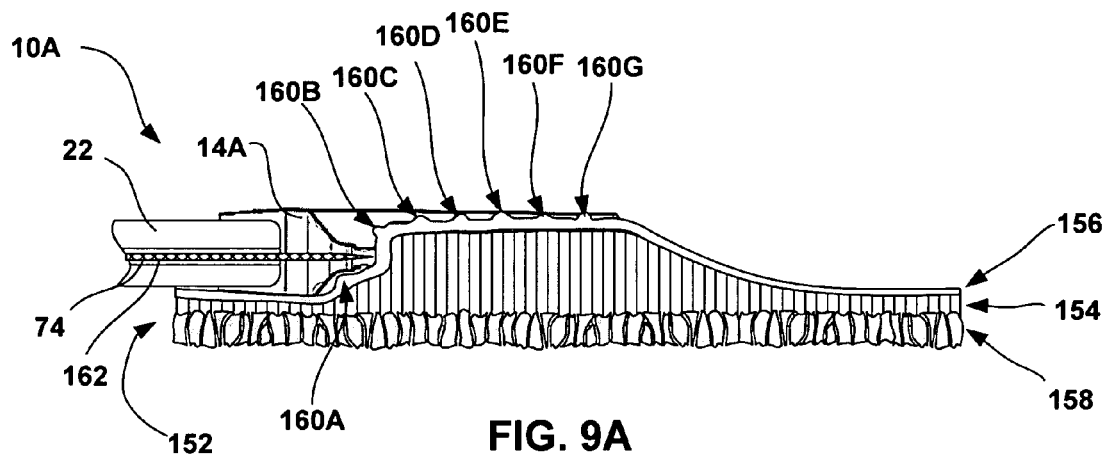
FIGS. 9A-9E are cross-section side view diagrams illustrating an example technique for delivery of tools and materials to selected tissue using the endoscopic delivery system of FIGS. 1 and 2.
Figure 9B:
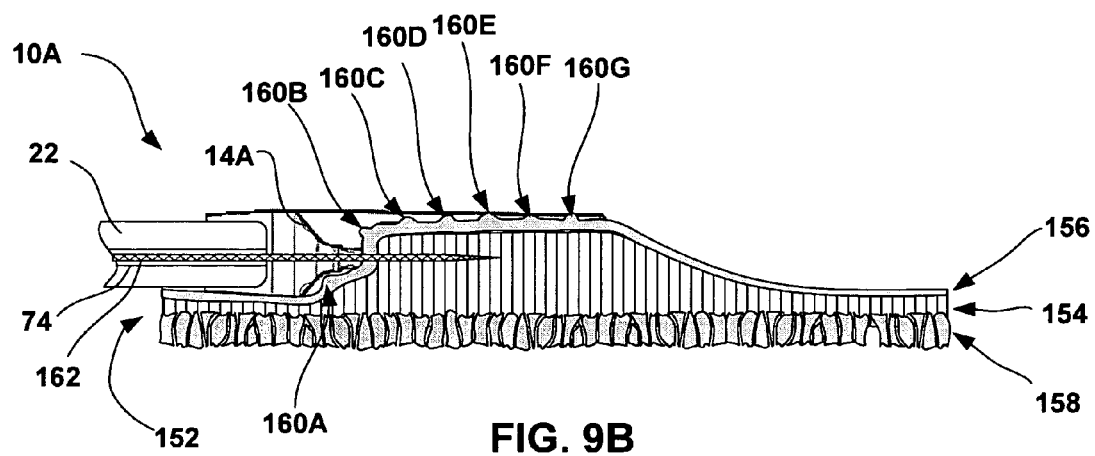

With the portion of luminal wall 152 drawn into tissue-receiving space 54, the user advances a needle 162 through working channel 74, substantially conical passageway 92 and delivery port 84, and into the tissue captured by tissue-receiving space 54, as shown in FIG. 9B. Needle 162 may be made resilient in an axial direction and bendable in a transverse direction to allow needle 162 to be advanced through working channel 74, substantially conical passageway 92, and delivery port 84. The bendability of needle 162 in the transverse direction may allow the needle to be guided by wall 94 of passageway 92 into delivery port 84 as it is advanced. Needle 162 may be formed of any of the polymers discussed above with reference to tissue-receiving member 14A and flexible probe 22, or may take the form of a elongated member including a lumen formed of any of those polymers with a distal portion formed of stainless steel, titanium, or the like.

Figure 9C:
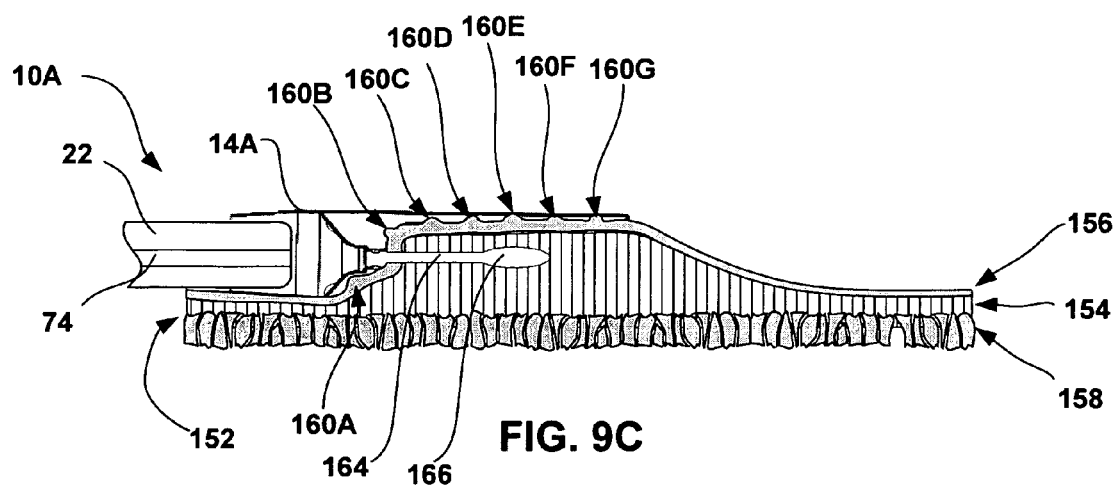

As shown in FIG. 9B, needle 162 is advanced into tissue-receiving space 54 along a path that is substantially parallel to luminal wall 152. However, as shown in FIGS. 9A-9D, a sufficient amount of luminal wall 152 is drawn into tissue-receiving space 54 such that the distal end of needle 162 extends to a location within submucosal layer 154. In some embodiments, as shown in FIG. 9C, needle 162 may inject a fluid, such as saline, to form an implantation pocket 166 within submucosal layer 154.

Figure 9D:
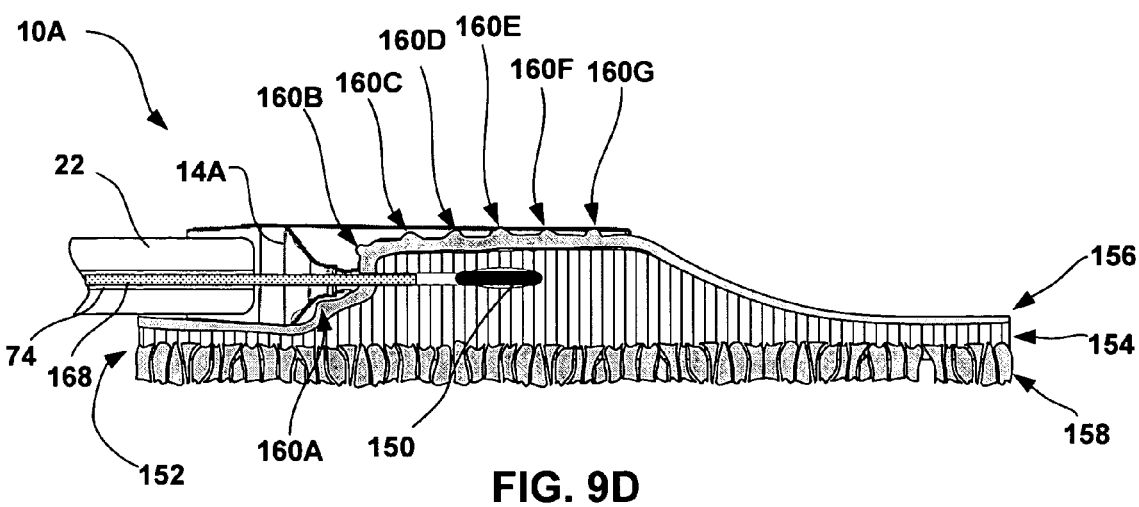

The user withdraws needle 162 from working channel 74, and inserts bulking device 150 into the working channel. The physician pushes bulking device 150 through hole 164 and into implantation pocket 166 with pushrod assembly 168, as shown in FIG. 9D. Pushrod assembly 168 may an elongated member that is resilient in an axial direction and bendable in a transverse direction to allow the pushrod assembly to be advanced through working channel 74, substantially conical passageway 92, and delivery port 84. The bendability of pushrod assembly 168 in the transverse direction may allow the pushrod assembly to be guided by wall 94 of passageway 92 into delivery port 84 as it is advanced. Pushrod assembly 168 may be formed of, for example, any of the polymers discussed above with reference to tissue-receiving member 14A and flexible probe 22.

If tissue is insufficiently captured by tissue-receiving space 54, the distal ends of needle 162 and pushrod assembly 168 may extend to an unintended location. Consequently, visualization of blebs 160 may allow a user of system 10A to avoid advancing the needle or pushrod assembly to an unexpected location. The size of tissue-receiving space 54 and location of delivery port 84 may be selected to control the location within captured tissue that tools and materials are delivered, e.g., depth or layer within luminal wall 152 to which needle 162, pushrod assembly 168 and bulking device 150 are delivered.

Figure 9E:
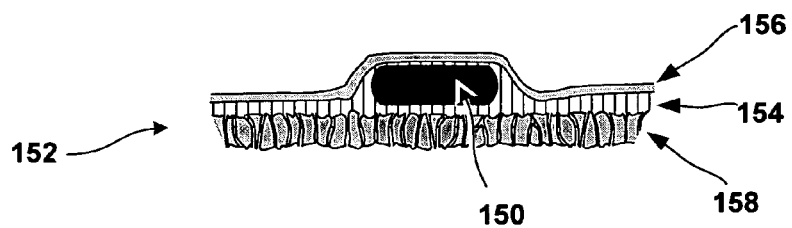

When implanted, bulking device 150 is in an unexpanded state. As shown in FIG. 9E, flexible probe 22 and tissue-receiving member 14A may be withdrawn following implantation of bulking device 150. Over time, bulking device 150 expands, e.g., due to absorption of fluid from the body of patient 18. In its expanded state, bulking device 150 provides a desired degree of tissue bulking.

Figure 10:
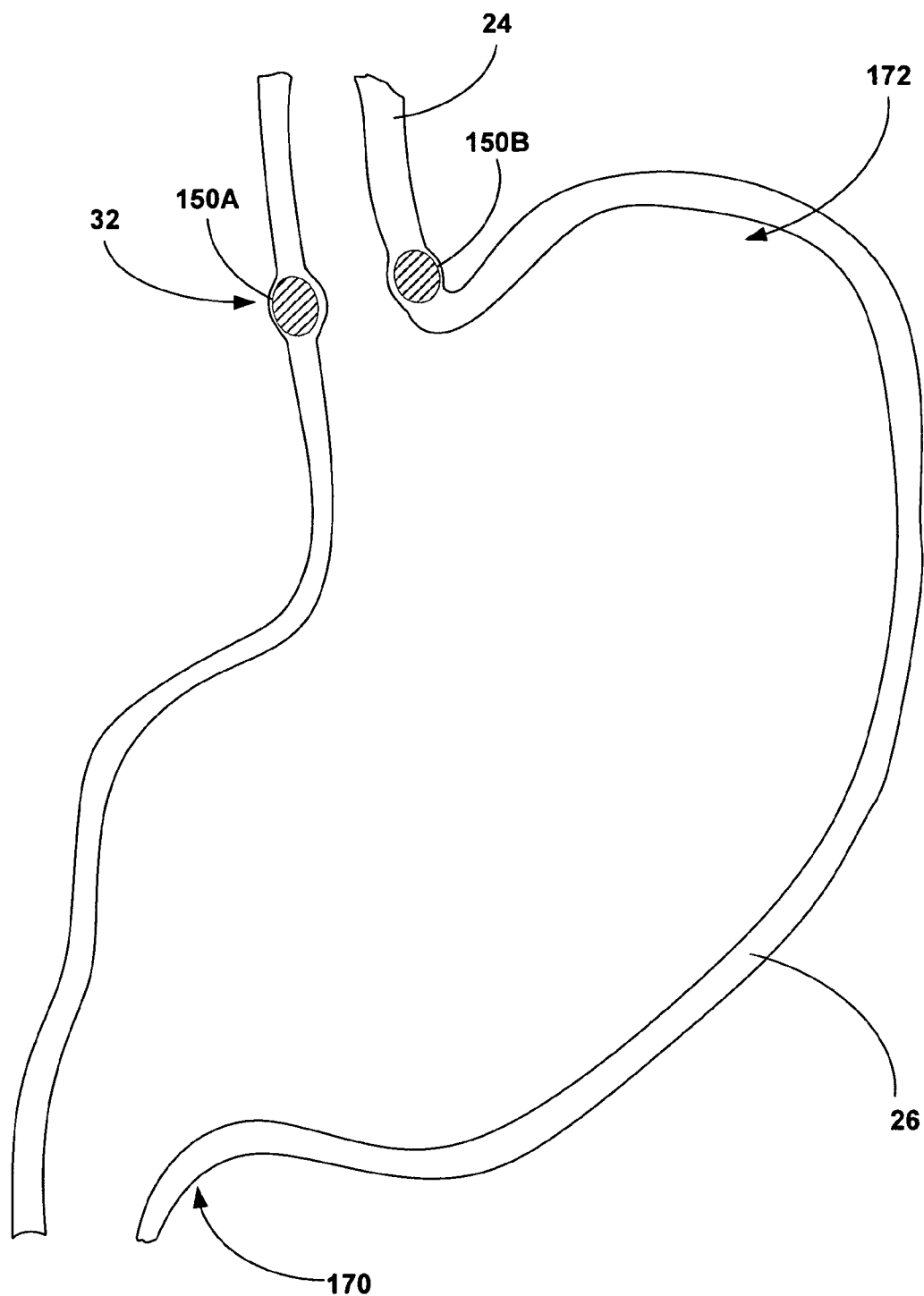
FIG. 10 is a conceptual diagram illustrating bulking devices implanted proximate to a lower esophageal sphincter (LES) of a patient.

FIG. 10 is a conceptual diagram illustrating bulking devices 150A and 150B (collectively "bulking devices 150") implanted proximate to LES 32 of patient 18. Bulking devices 150 may be implanted, for example, using endoscopic delivery system 10A and the techniques described above with reference to FIGS. 9A-9E.

Bulking devices 150 may be implanted proximate to LES 32 to treat GERD. When implanted proximate to LES 32, bulking devices 150 cooperate with the LES to increase its closing pressure, thereby reducing the likelihood of reflux flow of fluid from stomach 26 into esophagus 24. Bulking devices 150 may also interact with a flap valve (not shown) within stomach 26 near LES 32 or cause fibrosis within or near LES 32, which may further reduce the likelihood of reflux fluid flow. Although FIG. 1 illustrates two bulking devices 150 in cross-section, a single bulking device 150 may be implanted at LES 32, or, preferably, additional bulking devices may be implanted at LES 32 at different angular positions about esophagus 24 to form a ring-like arrangement of bulking devices for treatment of GERD.

However, the invention is not limited to implantation of bulking devices 150 proximate to LES 32 or treatment of GERD. To treat obesity, for example, a system 10 according to the invention may be used to implant bulking devices 150 some distance above LES 32 to form an obstruction of esophagus 24, proximate to pyloric sphincter 170 to impede emptying of stomach 26, or within a fundal region 172 of stomach 26 to bias stretch receptors and provide a sensation of satiety. Further, bulking devices 150 may bulk luminal walls other than the walls of esophagus 24 and stomach 26. For example, bulking devices 150 may be implanted proximate to a urethral sphincter of a urethral wall, or proximate to an anal sphincter to bulk an anal or rectal wall, to treat incontinence. Moreover, the invention is not limited to implantation of bulking devices 150 to bulk luminal walls. Bulking devices 150 may be implanted within tissue of any structure within a patient to bulk the structure.

Figure 11:
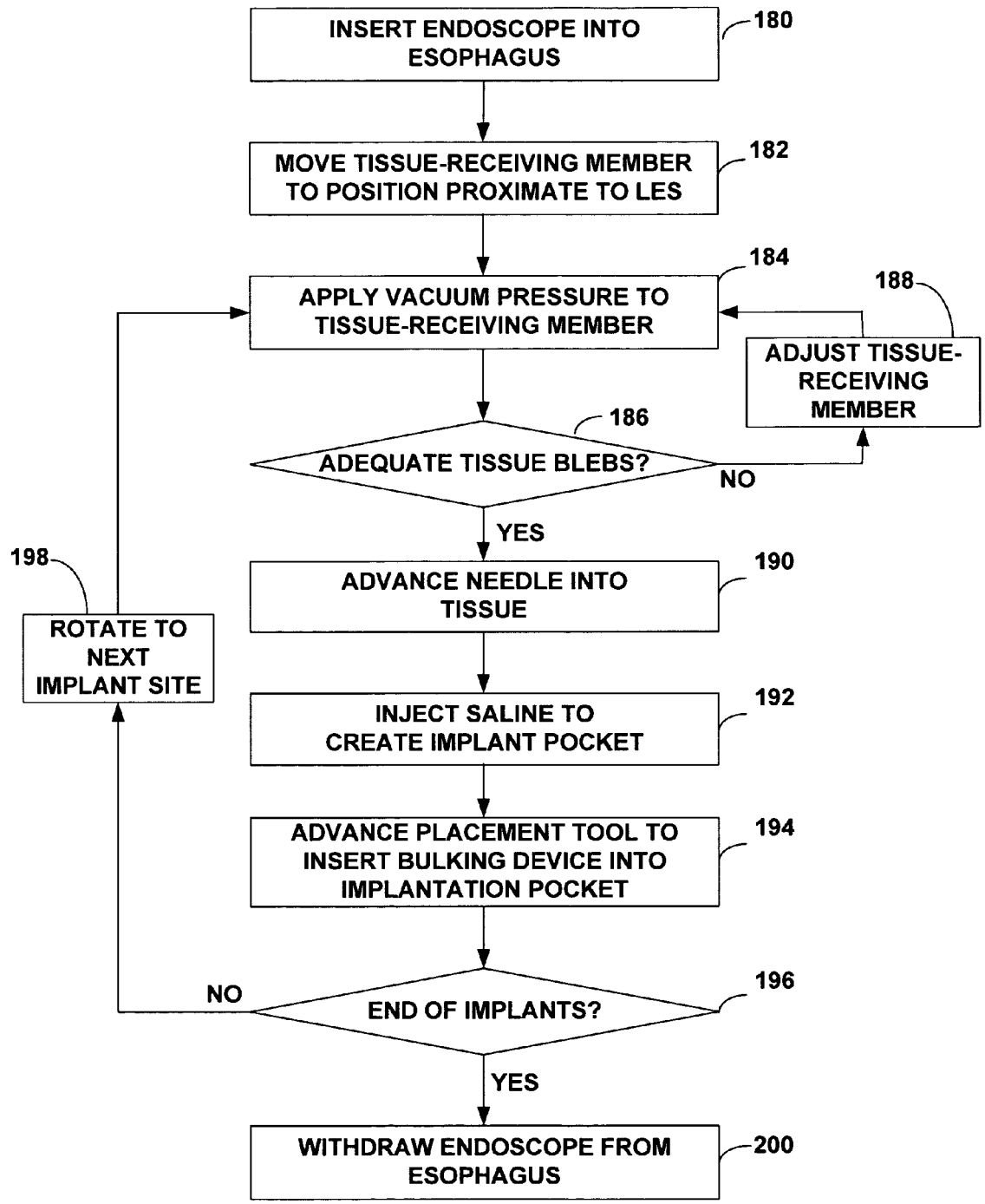
FIG. 11 is a flow diagram illustrating an example technique for implanting bulking devices using an endoscopic delivery system according to the invention.

FIG. 11 is a flow diagram illustrating an example technique for implanting bulking devices 150 proximate an LES of a patient using an endoscopic delivery system 10 according to the invention. As shown in FIG. 11, a user inserts endoscope 12 and, more particularly, flexible probe 22 of the endoscope, into esophagus 24 of patient 18 (180), and moves a tissue-receiving member 14 to a position proximate to LES 32 (182). The user then applies vacuum pressure to the tissue-receiving member 14 via vacuum lumen 72 of flexible probe 22 to draw a portion of the wall of esophagus 24 into a tissue-receiving space 54 defined by the tissue-receiving member (184).

The user may then view tissue blebs 160 protruding through apertures 80, 82 formed in the tissue-receiving member 14 via lens 78 of endoscope 12 to determine whether the tissue is adequately captured within tissue-receiving space 54 (186). If the tissue is not adequately captured, the user may remove the vacuum pressure, adjust the position of tissue-receiving member 14 (188), and reapply vacuum pressure to the tissue-receiving member (184). If the tissue is adequately captured, the user may advance a needle 162 through working channel 74 of flexible probe 22, substantially conical passageway 92 and delivery port 84 of tissue-receiving member 14, and into the tissue captured by tissue-receiving space 54 (190). Needle 162 creates a hole 164 in the tissue, and once the distal end of the needle 162 is in place, the user may inject saline or another fluid to create an implantation pocket 166 (192).

The user then withdraws the needle, and deploys a pushing rod assembly 168 via the working channel, passageway and delivery port, which implants the bulking device 150 through the hole in the tissue and into the implantation pocket (194). If additional bulking devices 150 are to be implanted (196), the user repositions flexible probe 22 to another implant site (198) proximate to LES 32 and repeats the implantation process. When all bulking devices have been implanted, the physician withdraws the flexible probe 22 and tissue-receiving member 14 from the esophagus (200).

A bulking device 14, as described herein, preferably is soft and compliant to minimize trauma within a luminal wall upon implantation. The bulking device may be constructed from a variety of biocompatible polymeric materials. Again, the materials forming the bulking device may be expandable. In particular, as described herein, the bulking devices may be formed from an expandable hydrogel material. Suitable materials, including hydrogel materials, are described in U.S. Pat. No. 6,401,718 to Johnson et al., assigned to Medtronic Endonetics, Inc., and entitled "Submucosal esophageal bulking device," the entire content of which is incorporated herein by reference.

As alternatives, described in Johnson et al., bulking device 14 may take the form of a fluid-filled, flexible capsule, pillow or balloon made from elastomeric materials such as silicone, latex, urethane, and the like. Example fillers include biocompatible liquid or gel such as saline, silicone oil, DMSO, polyvinyl, pyrollidone and hydrogels. As a further alternative, the bulking device may be a unitary structure formed by molding, casting, stamping or the like. The unitary structure may be formed from hydrogel material, biocompatible foam material such as silicone foam or polyurethane foam, or a variety of biocompatible materials such as silicone, polyurethane, polysulfone, polyester, and the like. As described in Johnson et al., foam material may include outer skin of porous foam that facilitates tissue ingrowth.

As alternatives to implanted solid materials, bulking devices may be formed by injected fluids that form solids following injection. A variety of implanted solid materials and injected fluids suitable for formation of bulking devices form a partial obstruction of the esophagus, as described herein, are disclosed in U.S. Published Patent Application No. 20040019388, to Starkebaum, assigned to Medtronic, Inc. and entitled "Methods and implants for retarding stomach emptying to treat eating disorders," the entire content of which is incorporated herein by reference. Accordingly, bulking devices may refer to solid, semi-solid, or filled implants, or injected fluids that form solid or semi-solid bulking devices in situ.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems as described herein. Further, although the invention has been described primarily in the context of implantation of bulking devices, it is not limited to delivery of bulking devices, or even delivery of material. An endoscopic delivery system, tissue-receiving member, or method according to the invention may be used to deliver any material or tool to tissue of a patient.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention claimed is:

1. A tissue-receiving member for use with an endoscope in an endoscopic delivery system, the tissue-receiving member comprising:

a first portion that defines an opening configured to receive a distal end of the endoscope; and a second portion that extends axially relative to a major axis of the endoscope from a distal end of the first portion to a distal end of the tissue-receiving member, wherein a distal surface of the first portion and an inner surface of the second portion define a tissue-receiving space configured to receive tissue of a patient when vacuum pressure is applied to the tissue-receiving space via the endoscope while the distal end of the endoscope is received in the opening of the first portion, wherein the distal surface of the first portion is formed with at least one vacuum aperture and at least one delivery port, the at least one delivery port substantially between the inner surface of the second portion and the at least one vacuum aperture of the distal surface, and wherein the tissue-receiving member is configured to transmit vacuum pressure received from a vacuum source through a vacuum port and a vacuum lumen of the endoscope to the tissue receiving space via the at least one vacuum aperture when the endoscope is received in the opening of the first portion.

2. The tissue receiving member of claim 1, wherein the at least one vacuum aperture and the at least one delivery port are configured for delivery of a tool through the at least one delivery port while vacuum pressure is applied via the at least one vacuum aperture.

3. A tissue-receiving member for use with an endoscope in an endoscopic delivery system, the tissue-receiving member comprising:

a first portion that defines an opening configured to receive a distal end of the endoscope; and a second portion that extends axially relative to a major axis of the endoscope from a distal end of the first portion to a distal end of the tissue-receiving member, wherein the major axis of the endoscope comprises a longitudinal axis of a distal portion of the endoscope, wherein a distal surface of the first portion and an inner surface of the second portion define a tissue-receiving space configured to receive tissue of a patient when vacuum pressure is applied to the tissue-receiving space via the endoscope while the distal end of the endoscope is received in the opening of the first portion, wherein the inner surface of the second portion is formed with a plurality of vacuum apertures, wherein the tissue-receiving member is configured to transmit vacuum pressure received from a vacuum source through a vacuum port and a vacuum lumen of the endoscope to the tissue receiving space via the plurality of vacuum apertures when the endoscope is received in the opening of the first portion, wherein the inner surface is oriented at a nonzero angle relative to the major axis of the endoscope in a direction substantially parallel to the major axis of the endoscope, wherein at least one of the plurality of vacuum apertures is located at approximately a distal end of the second portion, wherein a distance between the inner surface and the major axis in a direction orthogonal from the major axis increases moving distally along the major axis along substantially the entire length of the inner surface between the distal surface of the first portion and the distal end of the second portion, and wherein the nonzero angle provides a view of a bleb protruding through the vacuum aperture located at approximately the distal end of the second portion via a viewpoint located at the distal end of the endoscope when additional blebs are protruding through each of the plurality of vacuum apertures.

4. The tissue-receiving member of claim 3, wherein the angle is greater than approximately 1 degree.

5. The tissue receiving member of claim 1, wherein a depth of the second portion in a transverse direction relative to the major axis is less than a diameter of the endoscope along substantially an entire length of the second portion.

6. The tissue-receiving member of claim 5, wherein the depth of the second portion is less than approximately 65 percent of the diameter of the endoscope.

7. The tissue-receiving member of claim 5, wherein the depth of the second portion is within a range from approximately 4 millimeters to approximately 8 millimeters.

8. The tissue-receiving member of claim 1, wherein the tissue-receiving member includes a substantially conical passageway from the distal end of the endoscope to the at least one delivery port, wherein a diameter of the substantially conical passageway tapers toward the at least one delivery port.

9. The tissue-receiving member of claim 8, wherein a wall of the substantially conical passageway is substantially transparent.

10. The tissue-receiving member of claim 8, wherein a diameter of a proximal portion of the substantially conical passageway is substantially equal to a diameter of the distal end of the endoscope.

11. The tissue-receiving member of claim 1, wherein the inner surface of the second portion is formed with a plurality of vacuum apertures, and wherein the tissue-receiving member is configured to transmit vacuum pressure received from the vacuum source through the vacuum port and the vacuum lumen of the endoscope to the tissue receiving space via the plurality of vacuum apertures when the endoscope is received in the opening of the first portion.

12. The tissue-receiving member of claim 11, wherein the inner surface of the second portion is oriented at a nonzero angle relative to the major axis of the endoscope in a direction substantially parallel to the major axis of the endoscope, and wherein a distance between the inner surface and the major axis in a direction orthogonal from the major axis increases moving distally along the major axis along substantially an entire length of the inner surface between the distal surface of the first portion and the distal end of the second portion.

13. The tissue-receiving member of claim 12, wherein the nonzero angle is greater than approximately 1 degree.

14. The tissue-receiving member of claim 11, wherein the plurality of vacuum apertures are arranged in a non-axial pattern relative to the major axis of the endoscope, the major axis of the endoscope comprising a longitudinal axis of a distal portion of the endoscope.

15. The tissue-receiving member of claim 1, wherein the inner surface of the second portion is concave in at least a transverse direction relative to the major axis of the endoscope.

16. The tissue-receiving member of claim 1, wherein the at least one delivery port comprises a delivery port that is sized to receive a bulking device.

17. The tissue-receiving member of claim 1, wherein a distal end of the second portion defines an opening to the tissue-receiving space.

18. The tissue-receiving member of claim 1, wherein a distal end of the second portion includes a wall that extends substantially perpendicularly from the distal end.

19. The tissue-receiving member of claim 1, wherein the first portion is sized such that a proximal end of the first portion is located within the patient when the endoscope is advanced into the patient.

20. The tissue-receiving member of claim 1, wherein the first portion comprises an overtube that receives the endoscope, and the overtube is sized such that a proximal end of the overtube is located outside of the patient when the endoscope is advanced into the patient.

21. The tissue-receiving member of claim 3, wherein a depth of the second portion in a transverse direction relative to the major axis is less than a diameter of the endoscope along substantially an entire length of the second portion.

22. The tissue-receiving member of claim 21, wherein the depth of the second portion is less than approximately 65 percent of the diameter of the endoscope.

23. The tissue-receiving member of claim 21, wherein the depth of the second portion is within a range from approximately 4 millimeters to approximately 8 millimeters.

24. The tissue-receiving member of claim 3, wherein the tissue-receiving member is formed with at least one delivery port through the distal surface of the first portion and a substantially conical passageway from the distal end of the endoscope to the at least one delivery port, wherein a diameter of the substantially conical passageway tapers toward the at least one delivery port.

25. The tissue-receiving member of claim 24, wherein a wall of the substantially conical passageway is substantially transparent.

26. The tissue-receiving member of claim 24, wherein a diameter of a proximal portion of the substantially conical passageway is substantially equal to a diameter of the distal end of the endoscope.

27. The tissue-receiving member of claim 3, wherein the distal surface of the first portion is formed with at least one vacuum aperture and at least one delivery port, and wherein the tissue-receiving member is configured to transmit vacuum pressure received from the vacuum source through the vacuum port and the vacuum lumen of the endoscope to the tissue receiving space via the at least one vacuum aperture when the endoscope is received in the opening of the first portion.

28. The tissue-receiving member of claim 27, wherein the at least one delivery port is substantially between the inner surface of the second portion and the at least one vacuum aperture of the distal surface.

29. The tissue-receiving member of claim 27, wherein the at least one delivery port comprises a delivery port that is sized to receive a bulking device.

30. The tissue-receiving member of claim 27, wherein the at least one vacuum aperture and at least one the delivery port are configured for delivery of a tool through the at least one delivery port while vacuum pressure is applied via the at least one vacuum aperture.

31. The tissue-receiving member of claim 3, wherein the plurality of vacuum apertures are arranged in a non-axial pattern relative to the major axis of the endoscope.

32. The tissue-receiving member of claim 3, wherein the inner surface of the second portion is concave in at least a transverse direction relative to the major axis of the endoscope.

33. The tissue-receiving member of claim 3, wherein the distal surface of the first portion is formed with at least one delivery port sized to receive a bulking device.

34. The tissue-receiving member of claim 3, wherein a distal end of the second portion defines an opening to the tissue-receiving space.

35. The tissue-receiving member of claim 3, wherein a distal end of the second portion includes a wall that extends substantially perpendicularly from the distal end.

36. The tissue-receiving member of claim 3, wherein the first portion is sized such that a proximal end of the first portion is located within the patient when the endoscope is advanced into the patient.

37. The tissue-receiving member of claim 3, wherein the first portion comprises an overtube that receives the endoscope, and the overtube is sized such that a proximal end of the overtube is located outside of the patient when the endoscope is advanced into the patient.

* * * * *